United States Patent [19]

Jones et al.

[11] Patent Number: 5,055,783
[45] Date of Patent: Oct. 8, 1991

[54] MAGNETIC FIELD STRENGTH INDICATOR FOR USE PRIOR TO A MAGNETIC PARTICLE INSPECTION PROCEDURE

[75] Inventors: William F. Jones; Alfred E. Hinton, both of Charlotte; Frederick M. Hibbert, Mooresville, all of N.C.; Ernest E. Jackson, York, S.C.

[73] Assignee: Westinghouse Electric Corp., Pittsburgh, Pa.

[21] Appl. No.: 402,575

[22] Filed: Sep. 5, 1989

[51] Int. Cl.$^5$ .................... G01N 27/84; G01R 33/12; G01R 35/00
[52] U.S. Cl. .................................... 324/216; 324/202
[58] Field of Search ....................... 324/202, 214–216; 73/1 R; 29/558

[56] References Cited

U.S. PATENT DOCUMENTS 4,133,227 1/1979 Crowe et al. .................... 29/558

FOREIGN PATENT DOCUMENTS 2119518 11/1983 United Kingdom ............... 324/216

*Primary Examiner*—Walter E. Snow
*Attorney, Agent, or Firm*—K. Bach

[57] ABSTRACT

A field strength indicator for a magnetic particle inspection process is used to determine field strength and direction sufficient to identify real flaws in a test piece. The field strength indicator is a substantially flat shim having at least one series of artificial flaws formed therein by electric discharge machining. The artificial flaws have a geometry which render them compatible with real flaws and thus enable the magnetic field strength and direction to be properly set for conducting a magnetic particle inspection procedure. The surface containing the artifical flaws must be covered with a thin inert and non-magnetic coating for proper operation.

12 Claims, 2 Drawing Sheets

MAGNETIC FIELD STRENGTH INDICATOR FOR USE PRIOR TO A MAGNETIC PARTICLE INSPECTION PROCEDURE

BACKGROUND OF THE INVENTION

1. Field of the Invention

The present invention relates generally to magnetic particle inspection (MPI) procedures for finding metallurgical flaws in steam turbine components and, more specifically, to a field strength indicator for testing magnetic field strength and direction prior to conducting an MPI.

2. Description of the Related Art

An MPI procedure involves magnetizing a part to be tested and then spraying the part with small magnetic particles. The basis behind performing MPI procedures is to have a magnetic field of sufficient strength oriented in the proper direction to find flaws. MPI works because the magnetic field (or flux) in the test part is disrupted at surface flaws and discontinuities. This disruption in the field results in flux leakage out of the surface of the part across the flaw or discontinuity trapping very small magnetic particles that are sprayed on the surface. Thus, MPI requires that the part being inspected be magnetic and that it be magnetized to a level that allows sufficient flux leakage around real flaws and discontinuities but not around false indications. The accepted terminology for this is field strength. Field strength must be sufficient to fully magnetize the part, in order to allow for leakage around flaws, without magnetically saturating any unflawed areas.

Field strength is critical to MPI in that if it is too weak indications will not be shown and if it is too strong, false indications will result. Field direction is also important in that it needs to be oriented as close as possible to perpendicular to the direction of the flaws. For these reasons, prior to MPI inspections, the magnetic field strength and direction are checked with a field strength indicator.

The field strength indicator is an important part of an MPI procedure in that it must attempt to simulate expected flaws in several different directions. This is necessary so that field strength and direction can be evaluated at the same time. Typical MPI field strength indicators are made by joining several "pie-shaped" pieces of carbon steel, usually eight, into a circle or octagon. A thin piece of non-magnetic material, usually copper about 0.010 inches thick, is then joined to one side of the circle. All joining is performed by brazing.

FIGS. 1 and 2 represent a typical pie-type field strength indicator as described above. FIG. 1 illustrates a field strength indicator 10 having eight carbon steel pie sections 12 which are brazed together to form artificial flaws 14 at the joints therebetween. The assembled pie sections 12 have a maximum diameter of about 1 inch and a thickness of about ¼ of an inch. A pair of non-ferrous trunions 16 and 18 are brazed or otherwise mechanically attached at diametrically opposite points for attaching a non-ferrous handle 20 of any suitable length. As shown in FIG. 2, a copper plate 21, which is about 0.01 inches thick, is connected to one surface of the pie sections.

One of the drawbacks to the pie-type field strength indicator is that the joints between the pieces of carbon steel are relatively wide, being on the order of 0.010 to 0.030 inches. These wide artificial flaws are easy to magnetize and show; however, they are not representative of real flaws. This is because field strengths sufficient to show the pie indications are not sufficient to show real service-induced flaws and cracks. Because of the problems associated with the standard pie field strength indicators, there is a need to develop a field strength indicator that more closely represents real flaws.

Another drawback to the pie indicator, as well as other commercial indicators, is the material from which they are made. They are generally made from carbon steel which has significantly different magnetic properties than many of the materials, such as alloy steels, used for steam turbine components. Carbon steel has a higher permeability which allows it to accept more flux than other materials. As a result, it is possible to show indications in carbon steel field indicators at field strength that would not show indications in alloy steels.

SUMMARY OF THE INVENTION

An object of the present invention is to provide a field strength indicator used in magnetic particle inspection in which real flaws are distinguished from false flaws.

Another object of the present invention is to provide a field strength indicator having artificial flaws that are very small and thus resemble real flaws that require detection in power generation equipment.

Another object of the present invention is to provide a field strength indicator with artificial flaws which minimize mechanical holding of magnetic particles and thus prevents false field measurements.

Another object of the present invention is to provide a field strength indicator for magnetic particle inspection which is made of the same material as that which is being inspected.

In a preferred embodiment, a field strength indicator for determining magnetic field strength and direction in conjunction with a magnetic particle inspection procedure includes a shim having flat opposite parallel surfaces, and a series of standard indications corresponding in size to standard sized flaws of a part to be tested, each indication of the series being an artificial flaw. Each artificial flaw must be produced by a method that leaves the smallest possible width while providing specific length and depth. Electric discharge machining is one such method, however, other methods may also be applicable, e.g., etching.

These, together with other objects and advantages, which subsequently will be apparent, reside in the details of construction and operation of the invention as more fully hereinafter described and claimed, reference being made to the accompanying drawings forming a part hereof, wherein like reference numerals refer to like parts throughout.

DETAILED DESCRIPTION OF THE PREFERRED EMBODIMENTS

Magnetic particle inspection, as is well known, can be performed on a wet or dry basis. On the wet bases, fluorescing magnetic particles are suspended in a carrier medium, such as oil or water, and then sprayed on a test piece that has been magnetized. A commercially available spray-on solution is sold by the Magnaflux Corporation as Magnaflux 14AM prepared bath suspension. When the solution is sprayed on, magnetic field will leak out at points of discontinuity trapping the particles. These particles can be seen with a black light to indicate the presence of flaws in the test piece.

Field strength indicators are generally used for calibrating purposes prior to the MPI to determine the strength of the magnetic field.

To develop a new indicator, consideration was given to all aspects of MPI and the types of flaws and discontinuities which need to be found. Typical operation-induced indications are very short and tight. These are particularly hard to find with conventional MPI field strengths, as determined with the pie gauges, because the amount of leakage flux across the flaw is very low. In ideal observation conditions, it may be possible to see these indications, but in real situations they go undetected. From experience with MPI of steam turbine components returned from service, very tiny artificial flaws are needed on a field strength indicator.

The present invention takes into account the characteristics of real flaws and discontinuities. Of primary importance in this development was to obtain a field strength indicator with standard indications of similar size to real indications that need to be detected in turbine components. The present invention includes standard indications of similar size to real indications, with the standard indications being formed by electric discharge machining (EDM). This method produces very tiny and shallow artificial flaws which match up well with real indications that need to be detected in turbine components.

Figure 3:
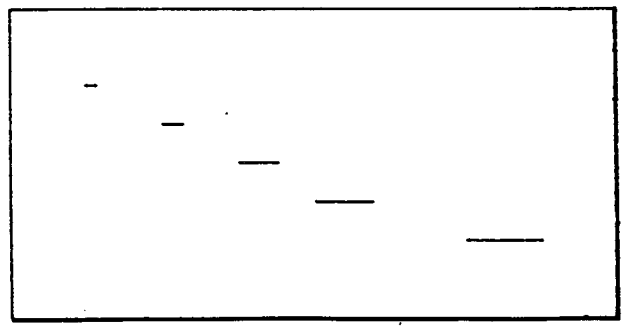
FIG. 3 is a top view showing development of the field strength indicator of the present invention.

FIG. 3 represents a "shim" indicator in which the notches have a depth of 0.002 inches. In arriving at the present invention, prototype shims were made in which the notch depth was varied between each shim, 0.002, 0.005 and 0.010 inches, but maintained constant on each shim. The notch lengths were selected based on typical reporting levels and sizes that could readily be seen.

The three shim indicators were evaluated by magnetizing a rotor using a head shot, i.e., passing current directly through the rotor, coil draping and using an electromagnetic yoke. Full wave rectified DC current was used for the head shot and coiled draping. AC and DC current was used with the yoke. The yoke leg spacing was about 8 inches.

To begin testing, all three shim indicators were sprayed with Magnaflux 14AM prepared bath suspension prior to application of any field. On indicators 0.005 and 0.010, the indications were visible. This appeared to be caused by the particles being held mechanically by the notches. On indicator 0.002, only the 3/32 and ⅛ long indications could be seen without application of the magnetic field. The mechanical holding effect was so strong on the 0.005 and 0.010 indicators that it was decided that the smaller depth was preferred.

FIG. 3 illustrates the indications as horizontal notches which range in length from 1/64 inch to ⅛ inch. Each notch is vertically spaced by 1/16 inch and spaced horizontally so that the beginning of each notch is 0.125 inches apart up to the 3/32 inch mark. The overall dimensions of the shim is 1 inch long and ½ inch wide.

The mechanical holding on the 0.002 inch indicator was much less than on the others but during the first series of tests it was discovered that it still occurred to an undesirable extent. Cleaning and demagnetizing could not completely eliminate the mechanical holding. To overcome the mechanical holding, the surface containing the notches was coated with a thin plastic sheet. The plastic sheet has to be very thin, on the order of 0.00025 to 0.001 inches thick, to provide the best indicator characteristics. To overcome the tendency for plastic to come off, the indicators are preferably sprayed with a clear lacquer to provide the necessary coating.

When testing the coated shim, favorable results were obtained. When a proper strength MPI field was applied, the indications could be readily seen.

When the field was turned off the indications held in place for a short time and then drained off the indicator. Such behavior is well suitable for a field strength indicator in that it allows for proper setting of the magnetic field strength without over magnetizing the part.

Figure 1:
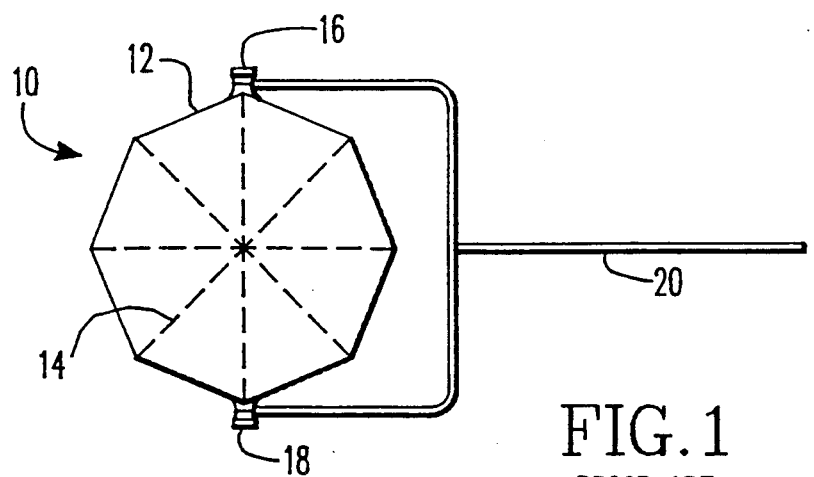
FIG. 1 is a top view of a known field strength indicator used for magnetic particle inspection.
Figure 2:
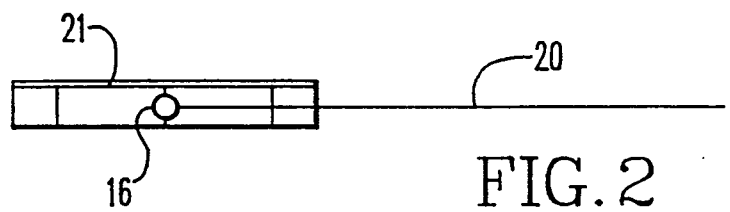
FIG. 2 is a side elevational view of the field strength indicator of FIG. 1.
Figure 4:
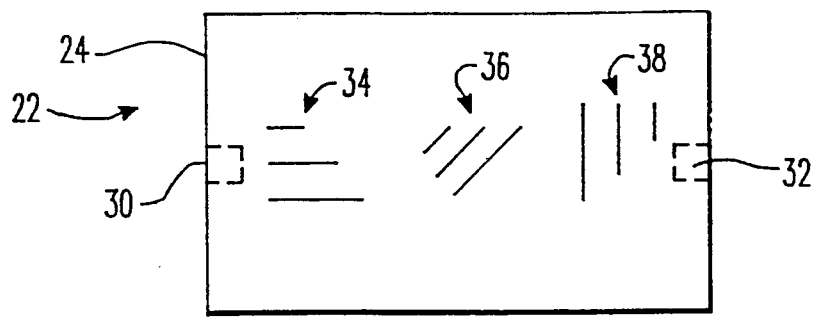
FIG. 4 is a top view of a first preferred embodiment of the field strength indicator according to the present invention.
Figure 5:
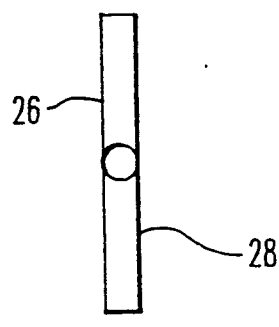
FIG. 5 is an end view of the field strength indicator of FIG..

FIGS. 4 and 5 represent a preferred embodiment of a field strength indicator (22) which includes a rectangular shim (24) having two flat opposite parallel surfaces (26) and (28). When testing the shim indicators as described with reference to FIG. 3, the indicators were made from very thin steel. Because of this, they were difficult to handle and position on the test piece. Thus, according to the preferred embodiment of FIGS. 4 and 5, the shim (24) has a thicker dimension so that it could be placed in a holder (not shown). A pair of holes (30) and (32) are formed longitudinally in the opposite end walls of the shim (24) to receive a holder generally of the type illustrated in FIG. 1.

Figure 6:
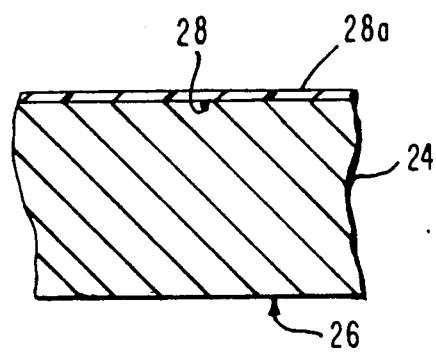
FIG. 6, is an enlarged sectional view of the shim 22, illustrating the coating 28a applied to the surface 28 having the notches formed therein.

FIG. 6 is an enlarged sectional view of the shim 22, illustrating the coating 28a applied to the surface 28 having the notches formed therein.

Artificial flaws are illustrated as a plurality of series of standard indications. The series (34) includes three parallel horizontal notches of varying length, but the same depth (0.002 inch) and the same width (0.0015 inch). The notch lengths are 1/64, 1/32, and 1/16 inch. The notch geometry is considered critical to obtaining adequate and accurate readings of magnetic field strength. Coating thickness is also critical and must be very thin and made from a non magnetic material to allow the indications to be magnetized properly.

A second series 36 of standard indications, three notches of the same dimensions as in the first series 34, but disposed at a 45° angle relative to the first series. A third series 38 is disposed at 45° relative to the second series 36 and 90° relative to the first series 34.

In order to practice the present invention, only one of the series need be provided at one time; however, although the first series could generate an indication of field strength in one direction, the device would have to be moved to indicate field strength in other directions. Thus, by providing a plurality of series which are oriented in different directions, multiple field directions can be measured at one time.

The notches of each series provide artificial flaws that are very small and resemble real types of indications that need to be detected in steam turbine components. The indications provided herein are substantially smaller than those found on the conventional field strength indicators, such as the pie indicator illustrated in Fig. 1. The size of the notches are such that they magnetically simulate real indications. This simulation makes it possible for the field strength and direction to be determined to yield the best sensitivity MPI.

Positioning of the field strength indicator 22 on the surface of the part is likewise critical. The field indicator needs to be placed in direct contact with the surface for proper measurement of the magnetic field strength. With the holder incorporated into the design of the indicator it can be held against the surface at the desired locations. Other thin foil type indicators require gluing or taping to the surface which can be difficult if the part is dirty.

In the shim indicator described herein, the coating of the notches is important It is necessary to insure that the notches do not mechanically hold the magnetic particles. If the coating is too thick, the leakage flux from the notches will not be sufficient to properly trap the magnetic particles The coating thicknesses need to be kept at a minimum, on the order of 0.0005 to 0.001. It is also important for the coating to be non-magnetic and to withstand any solvents or vehicles used during MPI.

In another embodiment, the shim indicator is coated with a thin chemically inert layer. An epoxy type paint with non-magnetic pigments would provide the layer.

Finally, the shim indicator of the present invention can be made of the same material being tested, and not necessarily made from high carbon steel. By using the same material as the part being tested, questions about permeability differences between the indicator and the test piece can be eliminated.

Another aspect of the present invention is to provide a method of forming artificial flaws in a field strength indicator. The method includes forming at least one series of parallel notches by electric discharge machining. The notches of each series are preferably of the same width and depth, and have variable lengths. Also in the preferred embodiment, when more than one series is used, the notches of each series are disposed in different directions.

Numerous alterations and modifications of the structure herein disclosed will suggest themselves to those skilled in the art. It is to be understood, however, that the present disclosure relates to the preferred embodiments of the invention which are for purposes of illustration only and are not to be construed as a limitation of the invention. All such modifications which do not depart from the spirit of the invention are intended to be included within the scope of the appended claims.

What is claimed is:

1. A field strength indicator for use prior to a magnetic particle inspection procedure employing a liquid, non-curable spray-on solution containing magnetic particles and a magnetized test piece, the indicator comprising:
   a shim having first and second flat opposite parallel surfaces; and
   at least one series of standard indications disposed in the same direction, formed in the first flat surface of the shim and corresponding in size to expected size flaws of a part to be tested, the shim being held in contact with the magnetized test piece at the second flat surface, to thereby impart an applied magnetic field from the test piece into the shim, each indication of the at least one series being an artificial flaw, said magnetic particles being trapped by the artificial flaws when a magnetic field of sufficient strength is applied to the test piece.

2. A field strength indicator as recited in claim 1, wherein the standard indications of the at least one series include a plurality of parallel notches formed in the one flat surface of the shim and having substantially the same depth and width, and having a different length.

3. A field strength indicator as recited in claim 2, wherein the at least one series includes a first series of parallel notches arranged horizontally on the one surface of the shim, a second series of parallel notches formed in the one flat surface of the shim at an angle relative to the parallel notches of the first series, and a third series of parallel notches formed in the one surface of the shim at an angle relative to the parallel notches of the first and second series.

4. A field strength indicator as recited in claim 1 further comprising, a thin coating covering the one surface of the shim having the at least one series of standard indications formed therein and providing means for preventing the standard indications from mechanically holding magnetic particles sprayed in the magnetic particle inspection procedure.

5. A field strength indicator as recited in claim 4, wherein the thin coating is inert to typical suspension medium, e.g., lacquer, epoxy, having a thickness ranging between about 0.0005 and 0.001 inch.

6. A field strength indicator as recited in claim 5, wherein the lacquer coating is non-magnetic.

7. A field strength indicator as recited in claim 1, wherein the shim includes two opposite end walls and the field strength indicator further includes a pair of mounting hole formed respectively in the two opposite end walls for receiving a holder.

8. A field strength indicator as recited in claim 3, wherein the parallel notches of each series include first, second and third notches, wherein the first notch is about 1/64 inch long, the second notch is about 1/32 inch long and the third notch is about 1/16 inch long.

9. A field strength indicator as recited in claim 1, further comprising a plurality of series of standard indicators formed in the finest flat surface, with at least two of the plurality of series of standard indicators being disposed in different directions from each other to provide an indication of field direction.

10. A field strength indicator as recited in claim 1, wherein the standard indicators are notches having a depth of about 0.002 inches (0.0508 mm).

11. A field strength indicator as recited in claim 10, wherein the notches of each at least one series have a length which varies in sequence, and the same depth.

12. A field strength indicator as recited in claim 11, wherein the depth of the notches is about 0.002 inches (0.0508 mm).

* * * * *